US00PP21928P2

(12) United States Plant Patent
Bradford

(10) Patent No.: US PP21,928 P2
(45) Date of Patent: May 24, 2011

(54) NECTARINE TREE NAMED 'MAY BRIGHT'

(50) Latin Name: *Prunus persica*
Varietal Denomination: May Bright

(76) Inventor: Lowell Glen Bradford, Le Grand, CA (US)

( * ) Notice: Subject to any disclaimer, the term of this patent is extended or adjusted under 35 U.S.C. 154(b) by 0 days.

(21) Appl. No.: 12/655,117

(22) Filed: Dec. 24, 2009

(51) Int. Cl.
*A01H 5/00* (2006.01)

(52) U.S. Cl. ..... Plt./190

(58) Field of Classification Search ..... Plt./190
See application file for complete search history.

(56) References Cited

U.S. PATENT DOCUMENTS

PP5,438 P 4/1985 Bradford
PP15,845 P2 7/2005 Bradford

*Primary Examiner* — Susan B McCormick Ewoldt

(57) ABSTRACT

The present invention relates to a new and distinct variety of nectarine tree, *Prunus persica,* broadly characterized by a medium size, moderately vigorous, hardy, self-fertile, productive and regular bearing tree. The variety blooms somewhat early and requires about 400 chilling hours. The fruit matures under the ecological conditions described in late May, with first picking on May 24, 2009. The fruit is uniformly medium to large in size for an early season variety, mildly acidic and sweet in flavor, globose in shape, clingstone in type, firm and melting in texture, yellow in flesh color, and mostly red in skin color.

1 Drawing Sheet

Botanical classification: *Prunus persica.*
Variety denomination: 'MAY BRIGHT'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'May Bright'.

The present variety was hybridized by me in 2003 as a first generation cross using an unnamed nectarine as the selected seed parent and an unnamed low chill nectarine as the selected pollen parent. However, this unnamed seed parent of the present variety was itself a first generation cross using 'Early Diamond' (U.S. Plant Pat. No. 5,438) nectarine as its seed parent and 'May Fire' (unpatented) nectarine as its pollen parent. The pollen parent of the present variety was developed by us as a seedling of an open pollinated low chill peach. The fruit of this cross was gathered in the spring of 2003, and the seeds were removed from the fruit, germinated using an embryo rescue technique, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2006 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed grandparent, 'Early Diamond' nectarine by producing nectarines that are mostly red in skin color, yellow in flesh color, clingstone in type, and mildly acidic in flavor, but is quite distinguished therefrom by producing fruit that is much larger in size, that is firmer, that is significantly less susceptible to split-pitting, and that matures about seven days earlier.

The present variety is similar to its pollen grandparent, 'May Fire' nectarine by producing nectarines that are firm, mostly red in skin color, yellow in flesh color, and clingstone in type, but is quite distinguished therefrom by requiring less chilling hours and by producing fruit that is larger in size, much less acidic in flavor, and that matures about twelve days later.

The present variety is most similar to 'Rose Bright' (U.S. Plant Pat. No. 15,845) nectarine by producing nectarines that are firm in texture, medium to large in size for the early season, acidic in flavor type, and nearly full red in skin color, but is distinguished therefrom by requiring less chilling hours and by producing fruit that is sweeter in flavor and that matures about ten days earlier.

SUMMARY OF VARIETY

In summary, the present variety is characterized by a medium size, moderately vigorous, hardy, self-fertile, productive and regular bearing tree. The variety blooms somewhat early and requires about 400 chilling hours. The fruit matures under the ecological conditions described in late May, with first picking on May 24, 2009. The fruit is uniformly medium to large in size for an early season variety, acidic and sweet in flavor, globose in shape, clingstone in type, firm and melting in texture, yellow in flesh color, and mostly red in skin color.

DRAWING

The accompanying photograph consists of four whole fruits positioned to display the characteristics of the skin color and form, one divided fruit to reveal the flesh and stone, two insets to reveal buds and a blossom, characteristic leaves, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of full ripe on Jun. 2, 2009, on the original tree during its sixth growing season. The blossom and flower descriptions were made the previous blooming season. All major color code designations are by reference to the Inter-Society Color Council, National Bureau of Standards. Common color names are also used occasionally.

Parentage

Seed parent: Unnamed nectarine.
Pollen parent: Unnamed low chill nectarine.

Tree

Size: Medium, reaching and maintaining a height of 12' [3.66 m.] and a spread of 10' [3.05 m.] after six growing seasons utilizing typical dormant pruning.
Vigor: Medium vigor, responding typically to irrigation and fertilization. The variety grows about 3' [0.91 m.] of surplus top-growth during the spring and summer. The plant should be grown on a standard commercial rootstock for production purposes.
Growth: Spreading and open.
Form: Vase type.
Hardiness: Half hardy with respect to central California winters.
Approximate chilling requirement: 400 hours.
Heat tolerance: Observed to perform adequately in typical central California climatic conditions, which typically include extended periods of heat.
Drought tolerance: Variety is developed for commercial orchards and requires regular irrigation.
Production: Very productive, thinning necessary.
Fertility: Self-fertile.
Bearing: Regular bearer with no alternate bearing yet observed.
Approximate chilling requirement: 400 hours.
Trunk:
- *Size.*—Medium, reaching a maximum diameter of 5" [127 mm.] after the sixth growing season.
- *Texture.*—Shaggy.
- *Bark color.*—A Grayish brown [61. gy.Br] and Grayish reddish brown [46. gy.rBr] variegation.
- *Lenticels.*—Approximate Number Per Square Inch: 15. Color: Dark orange yellow [72. d.OY]. Average Size: ¼" [6.4 mm.]. Shape: Eye-shaped, elongated.

Branches:
- *Size.*—Diameter of limb is 3½" [89 mm.] measured 12" above the crotch, 2¼" [57 mm.] measured 12" above the first fork.
- *Texture.*—Smooth on first year wood, increasing roughness with age.
- *Color.*—1st Year Wood Topside: Grayish red [19. gy.R]. 1st Year Wood Underside: Brilliant yellow green [116. brill.YG]. Second Year Wood: Strong brown [55. s.Br]. Older Wood: A Deep brown [56. deep Br] and Grayish brown [61. gy.Br] variegation.
- *Lenticels.*—Number Per Square Inch: About 70 on second year wood. Color: Light yellowish brown [76. l.yBr]. Average size: 1/16" [1.6 mm.] on second year wood. Shape: Eye-shaped, elongated.

Leaves:
- *Size.*—Medium. Average Length: 5½" [140 mm.]. Average Width: 1½" [38 mm.].
- *Arrangement.*—Alternate.
- *Thickness.*—Medium.
- *Form.*—Elliptical.
- *Apex.*—Acuminate.
- *Base.*—Acute, with an average base angle of 45 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Brilliant greenish yellow [98. brill.gY].
- *Petiole.*—Average Length: ½" [12.7 mm.]. Average Thickness: 1/16" [1.6 mm.]. Color: Light orange yellow [70. l.OY].
- *Stipules.*—Number: Usually 2 per leaf, up to 6 per growing tip. Average Length: ¼" [6.4 mm.]. Color: Brilliant yellow green [116. brill.YG] becoming Deep yellowish brown [75. deep yBr] with maturity.
- *Glands.*—Number: 2 to 4 per leaf. Position: Mostly alternate with a few opposite, located on petiole and base of blade. Size: Small. Form: Globose. Color: Moderate yellow green [120. m.YG] becoming Deep reddish brown [41. deep rBr] with age.
- *Leaf buds.*—Pointed, medium in size.

Flower buds:
- *Hardiness.*—Hardy, with respect to central California winters.
- *Diameter.*—Typically ⅜" [9.5 mm.] 1 week before bloom.
- *Length.*—Typically 9/16" [14.3 mm.] 1 week before bloom.
- *Form.*—Not appressed.
- *Surface.*—Pubescent.
- *Tip color.*—Light purplish pink [249. l.pPk].

Flowers: Perfect, complete, perigynous, usually a single pistil, about thirty stamens, five sepal and petal locations alternately positioned.
- *Type.*—Showy, large.
- *Average flower diameter.*—2" [50.8 mm.].
- *Number of petals.*—Usually five, about ten percent have extra petal fragments or double blossoms.
- *Petal shape.*—Circular to oval.
- *Petal margin.*—Entire, slightly wavy.
- *Average petal diameter.*—¾" [19.1 mm.].
- *Average petal length.*—¾" [19.1 mm.].
- *Petal apex.*—Rounded.
- *Petal base.*—Rounded to somewhat truncate.
- *Petal color.*—Pale pink [7. p.Pk] toward the apex, Strong pink [2. s.Pk] toward the base on both sides.
- *Anther color.*—Deep red [13. deep R] over a Light yellow [86. l.Y] center at bloom onset.
- *Stigma color.*—Pale yellow green [121. p.YG].
- *Sepal color.*—Dark purplish red [259. d.pR] on the outer surface.
- *Sepal length.*—¼" [6.4 mm.].

*Sepal width.*—3/16" [4.8 mm.].
*Sepal apex.*—Rounded to elliptical to match the sepal length and width.
*Sepal margin.*—Fairly smooth.
*Average pistil length.*—¾" [19.1 mm.].
*Average stamen length.*—9/16" [14.3 mm.].
*Fragrance.*—Moderate.
*Blooming period.*—Early, one week before 'Rose Bright' (U.S. Plant Pat. No. 15,845) nectarine.
*Onset of bloom.*—One percent on Feb. 14, 2009.
*Date of full bloom.*—Feb. 24, 2009.
*Duration of bloom.*—One to two weeks, dependent on ambient temperature.
*Number per cluster.*—1 to 3 with single flowers most common.

FRUIT

Maturity when described.—Full ripe, Jun. 2, 2009.
*Date of first picking: May* 24, 2009.
Date of last picking: Jun. 4, 2009.
Size: Uniform, medium to large for an early season variety.
*Average diameter axially.*—2⅜" [60.3 mm.].
*Average diameter across cheek plane.*—2¾" [69.9 mm.].
*Average diameter across suture plane.*—2 9/16" [65.1 mm.].
*Typical weight.*—5.5 ounces [156 grams].
Form: Variable, slightly asymmetrical.
*Longitudinal section form.*—Oblate.
*Transverse section through diameter.*—Round.
Suture: Extends from the base, along the side, and ends just past the pistil point.
*Near the base.*—A shallow groove.
*Along the side.*—A shallow trough.
*Near the apex.*—A shallow groove.
Ventral surface: Rounded, lipped throughout, but stronger toward the apex.
Lips: Slightly unequal.
Cavity: Flaring, elongated in the suture plane, suture showing on one side, Light yellow [86. l.Y] stem markings typical.
*Depth.*—⅜" [9.5 mm.].
*Breadth.*—¾" [19.1 mm.].
Base: Somewhat truncate, slightly cordate if viewed parallel to the suture.
Apex: Somewhat truncate, cordate if viewed parallel to the suture.
Pistil point: Apical, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Astringent.
*Tendency to crack.*—None observed.
*Color.*—Dark red [16. d.R] over a Very reddish orange [34. v.rO] background with Light orange yellow [70. l.OY] freckling toward the apex.
Flesh:
*Color.*—Brilliant yellow [83. brill.Y] with virtually no red streaking or bleeding.
*Surface of pit cavity.*—Covered with Very greenish yellow [97. v.gY] broken fibers when twisted from the stone.
*Amygdalin.*—Abundant to moderate.
*Juice.*—Moderate, rich.
*Texture.*—Very firm, melting.
*Fibers.*—Abundant, fine, tender.
*Ripens.*—Slightly earlier at the apex.
*Flavor.*—Mildly acidic and sweet, typically 16 brix.
*Aroma.*—Moderate.
*Eating quality.*—Excellent.

STONE

Type: Clingstone.
Form: Oval to somewhat obovate.
Hilum: Narrow, oval.
Base: Rounded.
Apex: Acuminate with a small, sharp 1/16" [1.6 mm.] tip.
Sides: Equal.
Surface: Irregularly furrowed and pitted throughout.
Ridges: Rounded.
External color: Moderate orange yellow [71. m.OY].
Pit wall color when cracked: Light orange [52. l.O].
Cavity surface color: Moderate orange [53. m.O].
Average pit wall thickness: 3/32" [2.4 mm.].
Average width: ⅞" [22.2 mm.].
Average length: 1 1/16" [27 mm.].
Average breadth: 9/16" [14.3 mm.].
Tendency to split: None observed.
Kernel:
*Form.*—Oval.
*Skin color.*—Pale greenish yellow [104. p.gY] when frist removed.
*Pellicle color.*—Strong yellowish brown [74. s.yBr].
*Vein color.*—Very greenish yellow [97. v.gY].
*Taste.*—Sweet.
*Viable.*—Only by using embryo rescue techniques.
*Average width.*—⅜" [9.5 mm.].
*Average length.*—9/16" [14.3 mm.].
*Amygdalin.*—Scant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is similar to 'Rose Bright' (U.S. Plant Pat. No. 15,845) nectarine by producing nectarines that are firm in texture, medium to large in size for the early season, acidic in flavor type, yellow in flesh color, and nearly full red in skin color, but is distinguished therefrom by requiring less chilling hours and by producing fruit that is sweeter in flavor and that matures about ten days earlier.

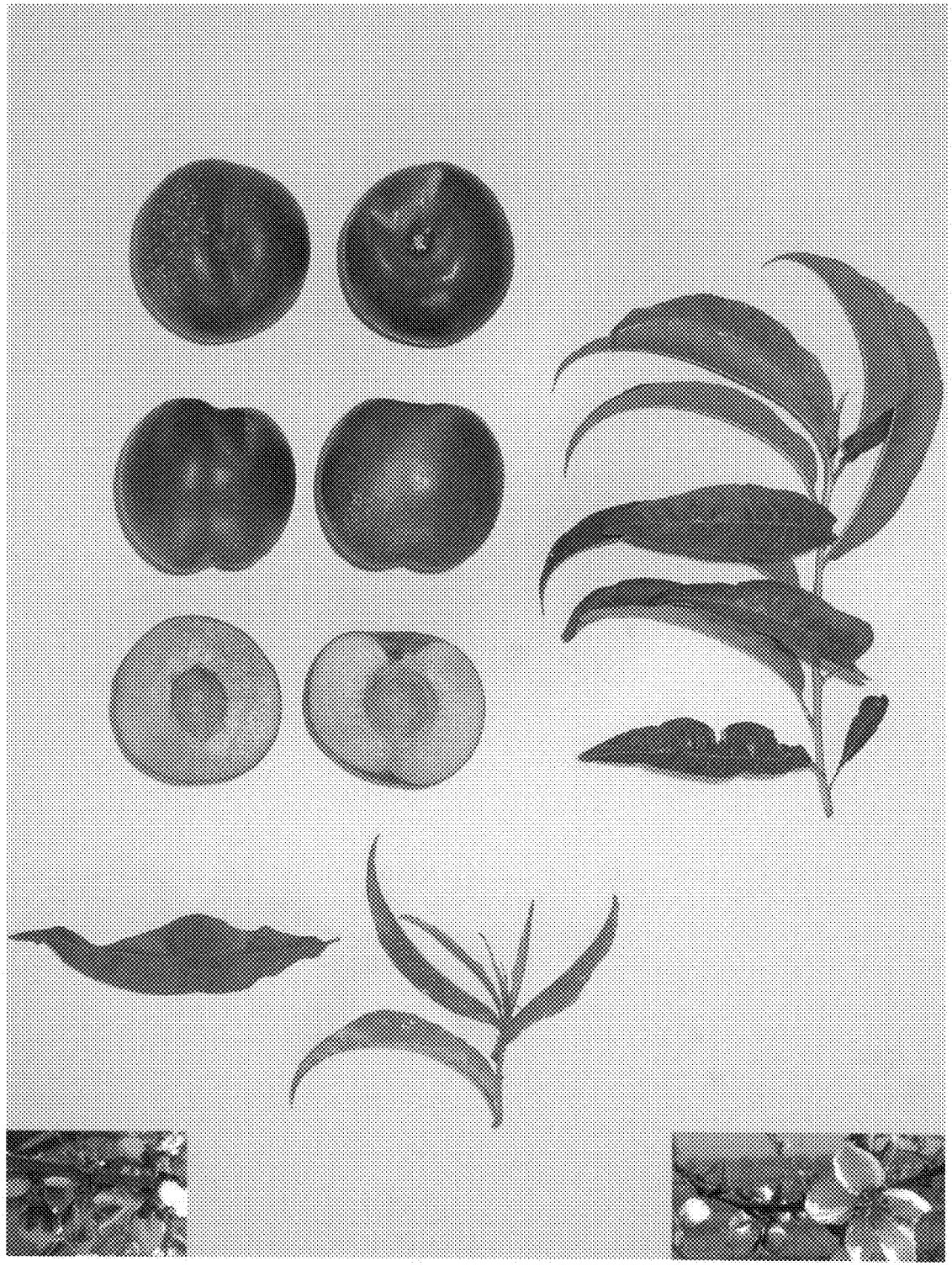

* * * * *